United States Patent [19]

Cullick et al.

[11] 4,455,860
[45] Jun. 26, 1984

[54] METHOD AND APPARATUS FOR DETERMINING CO2 MINIMUM MISCIBILITY PRESSURE OF RESERVOIR OIL

[75] Inventors: Alvin S. Cullick, Dallas; Melwyn L. Mathis, Arlington; Bert J. Warner, Dallas, all of Tex.

[73] Assignee: Mobil Oil Corporation, New York, N.Y.

[21] Appl. No.: 447,595

[22] Filed: Dec. 7, 1982

[51] Int. Cl.³ ............................................ G01N 33/26
[52] U.S. Cl. .................................... 73/19; 73/61.1 R
[58] Field of Search ........................ 73/19, 61.1 R, 53

[56] References Cited
U.S. PATENT DOCUMENTS

| 3,921,439 | 11/1975 | Burns | 73/61.1 R |
| 3,924,448 | 12/1975 | Howard | 73/61.1 R X |
| 4,117,727 | 10/1978 | Friswell | 73/19 |
| 4,236,404 | 12/1980 | Ketchum | 73/19 |
| 4,401,575 | 8/1983 | Stewart | 73/61.1 R X |
| 4,403,500 | 9/1983 | LeBaud | 73/19 |

Primary Examiner—Stephen A. Kreitman
Assistant Examiner—Vince Kovalick
Attorney, Agent, or Firm—Alexander J. McKillop; Michael G. Gilman; Lawrence O. Miller

[57] ABSTRACT

A method for determining the $CO_2$ minimum miscibility pressure (MMP) is disclosed which comprises filling a coiled capillary tube with oil at a predetermined temperature $T_1$ and an initial predetermined pressure $P_1$ less than the $CO_2$ MMP. Carbon dioxide is injected into the capillary tube at a fixed flow rate $F_1$ to displace the oil while maintaining the temperature of the oil at $T_1$ and the pressure at $P_1$. The pressure drop across the capillary tube and the volume of carbon dioxide injected is constantly measured. The pressure difference versus volume of carbon dioxide injected data is plotted and the pressure drop $\Delta P_1$ at the point of inflection where the second derivative goes from a negative value to a positive value is determined graphically. The previous steps are repeated while maintaining $T_1$ and $F_1$ constant at a different pressure $P_2$ less than the $CO_2$ MMP and $\Delta P_2$ at the inflection point of pressure versus volume of $CO_2$ injected is determined. Additional $CO_2$ displacement tests are conducted at the same temperature $T_1$ and $CO_2$ flow rate $F_1$ at various pressure levels (at least two) above the $CO_2$ MMP. The pressure drop at each pressure $P_3$ and $P_4$ above the $CO_2$ MMP is plotted versus the volume of carbon dioxide injected. The pressure drop $\Delta P_3$ and $\Delta P_4$ at the point of inflection as previously defined is determined for the corresponding pressure $P_3$ and $P_4$. The corresponding pressure drop at the inflection point obtained for the pressure values below MMP and the pressure drop at the inflection point obtained for the pressure values above MMP minus the pressure drop for $CO_2$ under the same test conditions as calculated by the Hagen-Poiseuille equation are plotted as a linear function of test pressure. The $CO_2$ MMP is determined graphically as the pressure at the point where the two lines defining miscible and immiscible displacement intersect.

19 Claims, 6 Drawing Figures

"PLUG-LIKE", OR MISCIBLE DISPLACEMENT-
SINGLE PHASE IN CONTACT ZONE;
NO OIL BEHIND CO₂ FRONT.

IMMISCIBLE DISPLACEMENT -
TWO PHASE FLOW BEHIND CO₂ FRONT
AND IN CONTACT ZONE.

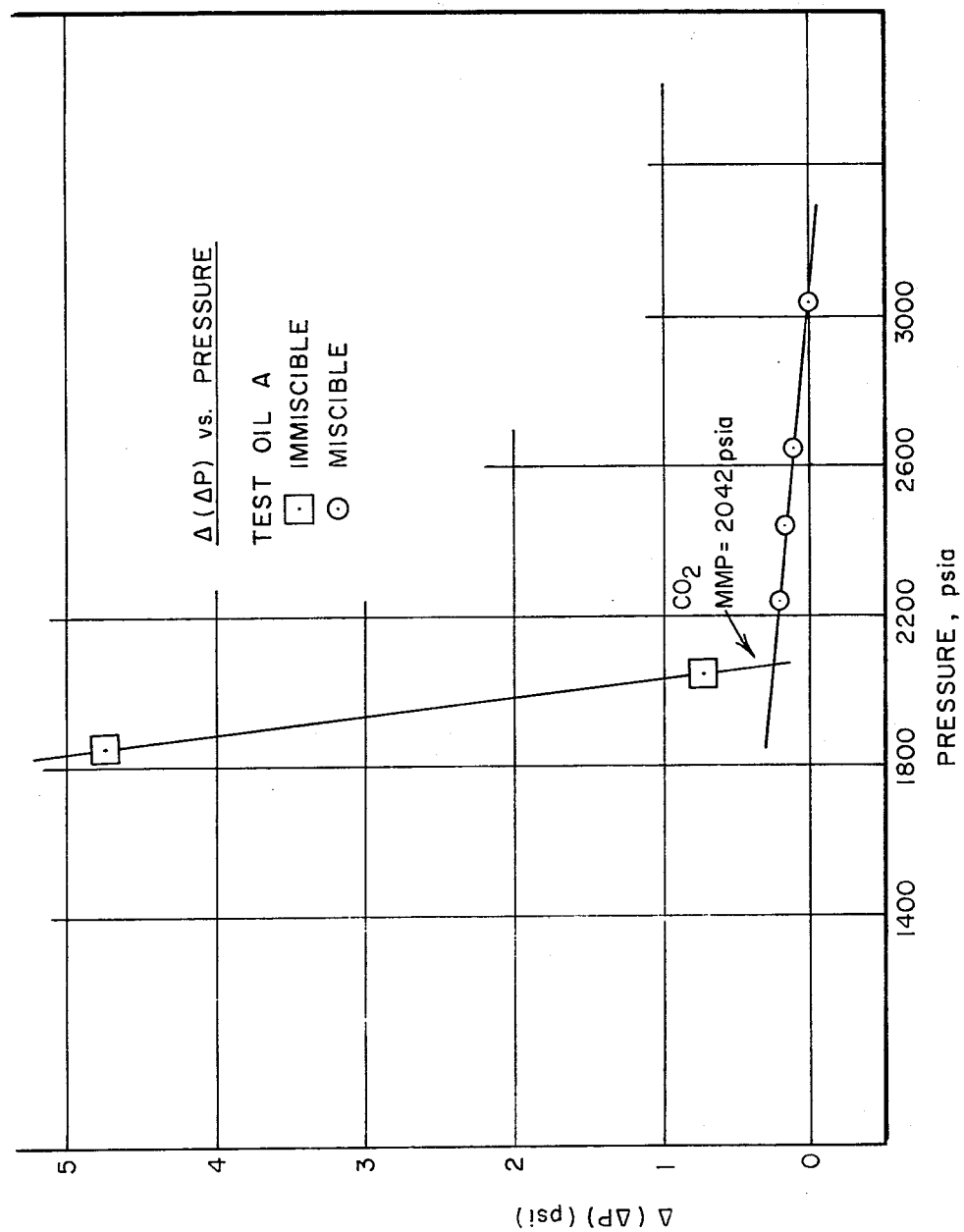

METHOD AND APPARATUS FOR DETERMINING $CO_2$ MINIMUM MISCIBILITY PRESSURE OF RESERVOIR OIL

FIELD OF THE INVENTION AND BACKGROUND OF THE INVENTION

1. Field of the Invention

This invention relates to an improved method and apparatus for determining the $CO_2$ minimum miscibility pressure (MMP) of reservoir oil displaced by carbon dioxide.

2. Background of the Invention

A variety of supplemental recovery techniques have been employed in order to increase the recovery of oil from subterranean reservoirs. These techniques include thermal recovery methods, waterflooding and miscible flooding.

In miscible flooding, the use of carbon dioxide has received considerable attention in the industry because of its high displacement efficiency and relatively low cost. Miscible recovery of a reservoir oil can be achieved by $CO_2$ displacement at a pressure level greater than a certain minimum, see Stalbergs, F. I., "Carbon Dioxide Miscible Flooding: Past, Present, and Outlook for the Future," J. Pet. Tech. (Aug. 1978) 1102–1112. This minimum pressure is defined as the carbon dioxide minimum miscibility pressure (MMP).

The slim tube method has been used on a routine basis in the oil industry for many years for measuring the $CO_2$ MMP of reservoir oil, see Yelling et al, "Determination and Prediction of $CO_2$ Minimum Miscibility Pressure," J. Pet. Tech. Vol. 32 (1), pg. 160 (1980).

In the slim tube method of measuring $CO_2$ MMP, the apparatus consists of a long, sand-packed column of 50–200 foot length coiled in an oven. The sand is saturated with reservoir fluid at the reservoir pressure. Carbon dioxide is injected at one end at a constant back pressure to displace the oil. Fluids produced from the column are separated into liquid and gas by blow-down to atmospheric pressure. The liquid oil is collected and weighed and the gas volume is measured. At pressures above the MMP, the ultimate recovery of reservoir oil is close to 100 percent, whereas below the MMP, the ultimate recovery is much less than 100 percent. A plot of the ultimate oil recovery versus test pressure has a discontinuity at the MMP. A typical slim tube determination of MMP by measuring recoveries at four different pressures requires eight days of experimentation.

The present invention provides an improved method and apparatus for determining $CO_2$ MMP that requires much less time than the slim tube test, e.g. one day compared to eight days, does not require handling any fluids during the experiment and the amount of reservoir oil required is about one-tenth that required for the slim tube.

SUMMARY OF THE INVENTION

The present invention involves a method and apparatus for determining the $CO_2$ minimum miscibility pressure (MMP) of a reservoir oil comprising conveying oil into the inlet end of an elongated capillary tube having a predetermined diameter and length until the tube is full of oil. The oil in the tube is initially maintained at a fixed temperature $T_1$ and a fixed pressure $P_1$ less than the MMP. Carbon dioxide is then injected into the inlet end of the tube at a fixed volumetric flow rate at room temperature, $F_1$, while maintaining the pressure on the oil in the tube at the value of $P_1$ and the temperature of the oil at $T_1$ thereby displacing oil through the tube. During carbon dioxide displacement the pressure drop across inlet and outlet ends of the tube is constantly determined along with the total volume of carbon dioxide injected into the tube. The pressure drop versus volume of carbon dioxide injected data is plotted and the pressure drop $\Delta P_1$ at the inflection point is graphically determined where the second derivative goes from a negative value to a positive value. The tube is cleaned with a solvent, dried with a purge gas, and evacuated. The tube is filled again with oil while maintaining the oil in the tube at the fixed temperature $T_1$ and a different pressure $P_2$ lower than the $CO_2$ MMP. Carbon dioxide is again injected into the inlet end of the tube at the flow rate of $F_1$ to displace the oil while maintaining the oil temperature at $T_1$ and the pressure at $P_2$. During injection of the carbon dioxide, the pressure drop across the tube and the total volume of carbon dioxide injected are constantly measured. The pressure drop versus volume of carbon dioxide injected data are plotted and the pressure drop $\Delta P_2$ at the point of inflection is graphically determined where the second derivative goes from negative to positive. The tube is again flushed with solvent, dried and evacuated. The tube is filled again with oil while maintaining the temperature at $T_1$ and a fixed pressure $P_3$ greater than the $CO_2$ MMP. Carbon dioxide is injected into the tube at the fixed volumetric flow rate $F_1$ to displace the oil while maintaining the oil temperature at $T_1$ and the pressure at $P_3$. During injection of the carbon dioxide at $P_3$, the pressure drop across the tube and the volume of carbon dioxide injected are constantly measured. The pressure drop versus volume of carbon dioxide injected data are plotted and the pressure drop $\Delta P_3$ at the point of inflection is graphically determined where the second derivative goes from negative to positive. The tube is flushed, dried, and evacuated and a fourth test is conducted by filling the tube with oil maintained at $T_1$ and a pressure $P_4$ greater than the $CO_2$ MMP. Carbon dioxide is injected at the flow rate $F_1$ to displace the oil while maintaining the oil temperature at $T_1$ and the pressure at $P_4$. During injection of carbon dioxide, the pressure drop across the tube and the volume of carbon dioxide injected are constantly measured. The pressure drop versus volume of carbon dioxide injected data are plotted and the pressure drop $\Delta P_4$ at the point of inflection is graphically determined where the second derivative goes from negative to positive. The pressure drop ($\Delta P$) for pure $CO_2$ flowing through the capillary tube under the same conditions of temperature, flow rate, and pressure is then determined using the following Hagen-Poiseille equation:

$$\Delta P_{CO2} = \frac{F_v(8)(\mu)(L)}{\pi (R^4)} \quad (1)$$

where
  $\Delta P_{CO2}$ = pressure drop across tubing;
  $F_v$ = volumetric flow rate.,
  $\mu$ = viscosity of $CO_2$ at test temperature and pressure;
  $L$ = capillary tube length;
  $R$ = capillary tube radius.

The pressure drop $\Delta P_1$ and $\Delta P_2$ minus the corresponding pressure drop for $CO_2$ under the same conditions as determined by equation (1) are plotted as a linear function of $P_1$ and $P_2$ for immiscible displacement and the pressure differences $\Delta P_3$ and $\Delta P_4$ minus the corresponding pressure differences for $CO_2$ are plotted as a linear function of $P_3$ and $P_4$ for miscible displacement. The $CO_2$ MMP is determined graphically as the pressure at the point where the two lines defining miscible and immiscible displacement intersect.

In accordance with the present invention there is provided an apparatus for determining the $CO_2$ minimum miscibility pressure (MMP) of a reservoir oil comprising an elongated capillary tube having an inlet end and an outlet end and means for supplying a stream of oil to the inlet end of the tube. An expansion chamber having a top and bottom is provided with conduit means for providing fluid communication between the top of the expansion chamber and the outlet end of the tube. Back pressure regulator means are provided in the bottom of the chamber for maintaining a predetermined pressure on the top of the chamber. Means are provided to maintain the tube at a constant temperature. Means are provided to inject carbon dioxide into the inlet end of the tube at a constant flow rate thereby displacing oil from the tube into the expansion chamber against a predetermined back pressure. Means are provided to constantly measure the pressure difference between the inlet and outlet ends of the tube along with means for measuring the total volume of carbon dioxide injected into the tubing.

DESCRIPTION OF THE DRAWINGS

FIG. 6 is a graph of the pressure drop across a capillary tube at various inflection points as determined from FIGS. 4 and 5 minus the pressure drop for $CO_2$ under the same conditions versus pressure for miscible and immiscible displacement wherein the $CO_2$ MMP is determined as the pressure at the point where the two lines defining miscible and immiscible displacement intersect.

DESCRIPTION OF THE PREFERRED EMBODIMENT

This invention relates to a method and apparatus for determining the $CO_2$ minimum miscibility pressure of reservoir oil displaced by carbon dioxide.

Figure 1:
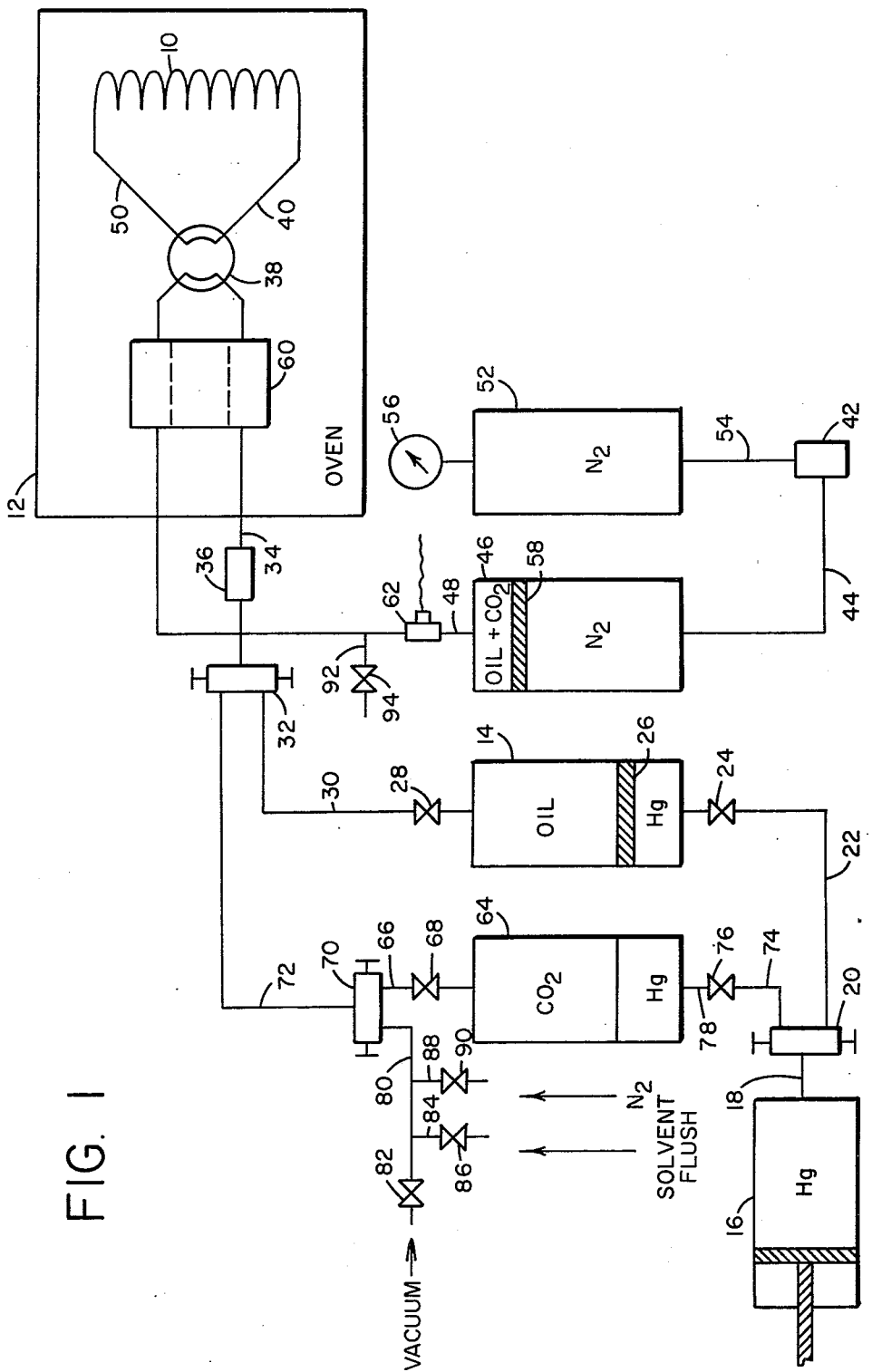
FIG. 1 is a diagrammatic illustration of a preferred embodiment of the apparatus used in this invention.

Referring to FIG. 1, a capillary tube 10 consisting of stainless steel tubing, preferably 0.032 cm. in diameter and 24 feet long is housed in an oven 12 capable of maintaining the temperature of the capillary tube at a constant value within the range of 80° to 250° F. The reservoir oil to be tested is delivered from vessel 14 to capillary tube 10 by means of a positive displacement pump 16. A suitable positive displacement pump is Model No. 2256 manufactured by Ruska Instrument Co., Houston, Tex. Mercury from pump 16 is displaced into line 18, through a three-way valve 20 positioned such that the mercury flows from line 18 into line 22. Mercury in line 22 is delivered to the lower portion of vessel 14 via valve 24 and displaces the reservoir oil contained therein by means of a floating piston 26 that responds to the pressure of the mercury below the piston. Capillary tube 10 may be filled with reservoir oil at the desired temperature and pressure by flowing the oil from vessel 14 through valve 28, through line 30, through three-way valve 32 positioned such that the oil flows from line 30 into line 34, through a filter 36 (7 microns) and then into a 4-port switching valve 38 connecting line 34 with the inlet end 40 of capillary tube 10. A suitable switching valve 38 is a 4 PORT V-4UT-UHPa-N60 valve, manufactured by Valco, Inc., P.O. Box 55603, Houston, Tex. 77055. The desired back pressure is maintained at the outlet 50 of capillary tube 10 by means of a gas dome-loaded back pressure regulator 42 provided with a gas reservoir vessel 52 and pressure gauge 56 containing pressurized nitrogen in fluid communication with the gas dome of the back pressure regulator via line 54. The back pressure regulator 42 is in fluid communication with the outlet 50 of capillary tube 10 via line 44, high pressure vessel 46, line 48 and switching valve 38 connecting line 48 with the outlet end 50 of the capillary tube. A suitable back pressure regulator 42 is Model No. 8908, manufactured by GROVE VALVE CO., Oakland, Calif. Pressurized nitrogen in line 44 exerts pressure on the bottom side of float 58 that rises and falls in vessel 46 in response to the changes in pressure. A differential pressure transducer 60 is in fluid communication with lines 34 and 48 that measures the pressure drop across the capillary tube 10. A suitable transducer 60 is a Sensotec transducer model A-5, 5 psid, manufactured by Sensotec, Inc., 1200 Chesapeake Ave., Columbus, Ohio 43212. Sensing element 62 is a pressure transducer in fluid communication with line 48 capable of providing a signal output which indicates whether the sensed pressure in system is above or below a reference pressure.

Carbon dioxide is supplied to capillary tube 10 from a high pressure vessel 64 through line 66, through open valve 68, through a three way - two stem valve 70 to a line 72, through three way - two stem valve 32 positioned such that the carbon dioxide flows into line 34. The carbon dioxide flows from vessel 64 into capillary tube 10 by means of the positive displacement pump 16. Mercury from pump 16 flows through line 18 and into three way - two stem valve 20 positioned such that the mercury flows into line 74, through open valve 76 and into the bottom of vessel 64 through line 78.

To clean out the entire tubing system and prepare it for the next experiment, the apparatus is provided with a line 80 in fluid communication with line 72 via valve 70. Line 80 is connected to a vacuum source through valve 82, a solvent flush line 84 through valve 86, and a source of nitrogen through valve 90. The solvent used for flushing the system exits through line 92 that branches off line 48 and provided with valve 94.

Vessels 14, 46, 52 and 64 are high pressure stainless steel vessels rated to 6000 pounds per square inch (psi) at 260° F.

The invention may be carried out by initially cleaning out the entire system by flushing it with a solvent such as pentane or chlorothane. During the flushing operation, valve 86 is opened and solvent is pumped into line 84, flows through line 80, through three-way valve 70 positioned such that the solvent flows from line 80 into line 72. The solvent then passes through three-way valve 32 positioned such that the solvent flows from line 72 into line 34, through four-way valve 38 actuated such that the solvent flows through the capillary tube 10, through line 48 and finally exiting through line 92 and opened valve 94. Thereafter, the system is dried by purging it with nitrogen by opening valve 90 and allowing nitrogen to flow through the system in the same manner as previously described for the solvent flush. The system is then evacuated by a vacuum source connected to line 80 through valve 82.

The tubing system is then filled with reservoir oil from vessel 14 until capillary tube 10 is filled with oil at a predetermined temperature and pressure. The pressure may vary from 1000 to 4000 psi. The oil from vessel 14 is pumped into capillary tube 10 by a positive displacement pump 16. The oil flows from vessel 14 through line 30, through three-way valve 32 positioned such that the oil flows from line 30 into line 34, through filter 36, through four-way valve 38 positioned such that the oil flows from line 34 into the inlet line 40 of capillary tube 10. The desired pressure on the outlet end 50 of the capillary tube 10 is maintained by means of back pressure regulator 42. The capillary tube 10 is confined within oven 12 that heats the oil in the capillary tube to the desired displacement temperature. Once the system is filled with oil and allowed to equilibrate at the desired displacement temperature and pressure, valve 38 is positioned such that the oil in capillary tube 10 is isolated from the remainder of the system.

The system is thereafter cleaned out by flushing it with a solvent such as pentane or chlorothane. During the flushing operation, valve 86 is opened and solvent is pumped into line 84, flows through line 80, through three-way valve 70 positioned such that the solvent flows from line 80 into line 72. The solvent then passes through three-way valve 32 positioned such that the solvent flows from line 72 into line 34, through four-way valve 38 actuated such that the solvent does not flow through the capillary tube 10, through line 48 and finally exiting through line 92 and opened valve 94. Thereafter, the system is dried by purging it with nitrogen by opening valve 90 and allowing nitrogen to flow through the system in the same manner as previously described for the solvent flush. The system is then evacuated by a vacuum source connected to line 90 through valve 82. The oil in capillary tube 10 remains isolated from the remainder of the system.

Figure 2:
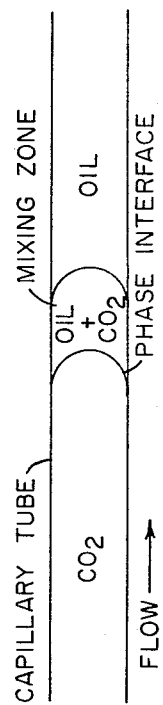
FIG. 2 is an illustration of $CO_2$ miscible displacement of reservoir oil in a capillary tube.
Figure 3:
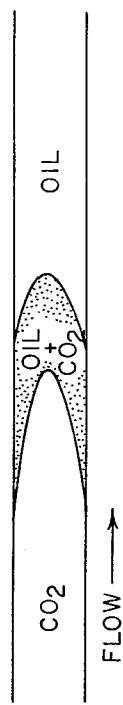
FIG. 3 is an illustration of $CO_2$ immiscible displacement of reservoir oil in a capillary tube.

Thereafter, carbon dioxide from vessel 64 is pumped into the inlet end 40 of capillary tube 10 at a constant volumetric flow rate at room temperature by means of positive displacement pump 16. The volumetric flow rate may vary from 0.97 to 2.34 cc/hr. The carbon dioxide flows from vessel 64, through line 66 via opened valve 68, through three-way valve 70 positioned such that the $CO_2$ flows from line 66 to line 72. The carbon dioxide then flows from line 72 through three-way valve 32 positioned such that the carbon dioxide flows from line 72 to line 34, and through four-way valve 38 positioned such that carbon dioxide flows from line 34 to the inlet end 40 of capillary tube 10. The carbon dioxide then flows through the capillary tube 10, displacing the oil therein, back through valve 38 positioned such that the oil displaced by carbon dioxide flows from the outlet end 50 of capillary tube 10 to line 48 and then into the top portion of high pressure vessel 46. As the carbon dioxide displaces oil through capillary tube 10, the movement of fluid through the capillary tube 10 creates a pressure drop across the length of the tube which is constantly measured by differential pressure transducer 60. This pressure drop is proportional to the viscosity of the fluid in the capillary tube 10. The carbon dioxide is introduced into capillary tube 10 at a constant volumetric flow rate which may vary from 1 cc/hr to 30 cc/hr at room temperature. The total volume of carbon dioxide pumped through the capillary tube 10 and into vessel 46 is measured. The pressure drop across the capillary tube 10 during $CO_2$ injection is constantly measured by differential pressure transducer 60 and recorded on a strip chart recorder (not shown) and plotted as a function of the volume of carbon dioxide injected. The actual pressure drop across capillary tube 10 is dependent on the type of oil being tested, flow rate, temperature, and pressure. For instance, when capillary tube 10 is filled with a typical reservoir oil the pressure difference is about 4 psid whereas when the tube is filled with carbon dioxide the pressure difference is about 0.2 psid for a flow rate of 2.34 cm$^3$ per hour. Thus, as carbon dioxide displaces oil, the pressure difference across tube 10 decreases from about 4 psid to about 0.2 psid, once all oil has been displaced from the tube. For pressures above the carbon dioxide minimum miscibility pressure (MMP), the displacement is "plug-like" as illustrated in FIG. 2 and the pressure drop across the tube 10 decreases as approximately a linear function of the volume of carbon dioxide injected into the tube. A plot of the function of pressure drop versus volume of carbon dioxide injected passes through an inflection point which occurs where the second derivative goes from a negative value to a positive value. For pressures below the $CO_2$ MMP, the displacement is not "plug-like" but a region of two phase flow is present between carbon dioxide and the oil as illustrated in FIG. 3. Thus, for immiscible $CO_2$ displacement the correlation between pressure drop and the volume of carbon dioxide injected is not a linear function. The pressure drop also passes through an inflection point as the volume of carbon dioxide increases for immiscible $CO_2$ displacement which occurs at the point where the second derivative of pressure drop vs. volume of carbon dioxide injected goes from negative to positive. The pressure drop at the inflection point is a function of the effective viscosity of the total fluids in the tube. The pressure drop at that point is proportional to the volume of test oil remaining in tube 10.

To determine the $CO_2$ MMP, the pressure drop at the point of inflection is first corrected by subtracting the pressure drop for pure carbon dioxide under the same conditions of temperature, flow rate, and pressure. The corrected pressure drop at the inflection point is plotted as a linear function of pressure for at least two different pressures above and below the $CO_2$ MMP. The $CO_2$ MMP is then determined graphically as the pressure at the point where the two lines which define miscible and immiscible displacement intersect. The $CO_2$ MMP represents the lowest pressure at which miscible displacement occurs.

The method of our invention will be further illustrated by the following specific example:

EXAMPLE

In order to determine the $CO_2$ MMP for a given test oil at a fixed temperature and a fixed volumetric flow rate at room temperature, $CO_2$ displacement tests were conducted at various pressure levels above and below the $CO_2$ MMP on a test oil A from the Postle Upper Morrow sands in the panhandle of Oklahoma. All tests were conducted on the test oil at a temperature of 147° F. and a $CO_2$ volumetric flow rate of 2.34 cc per hour at room temperature, 78° F. The capillary tubing 10 was stainless steel, 24 feet long and 0.032 cm. in diameter.

Figure 4:
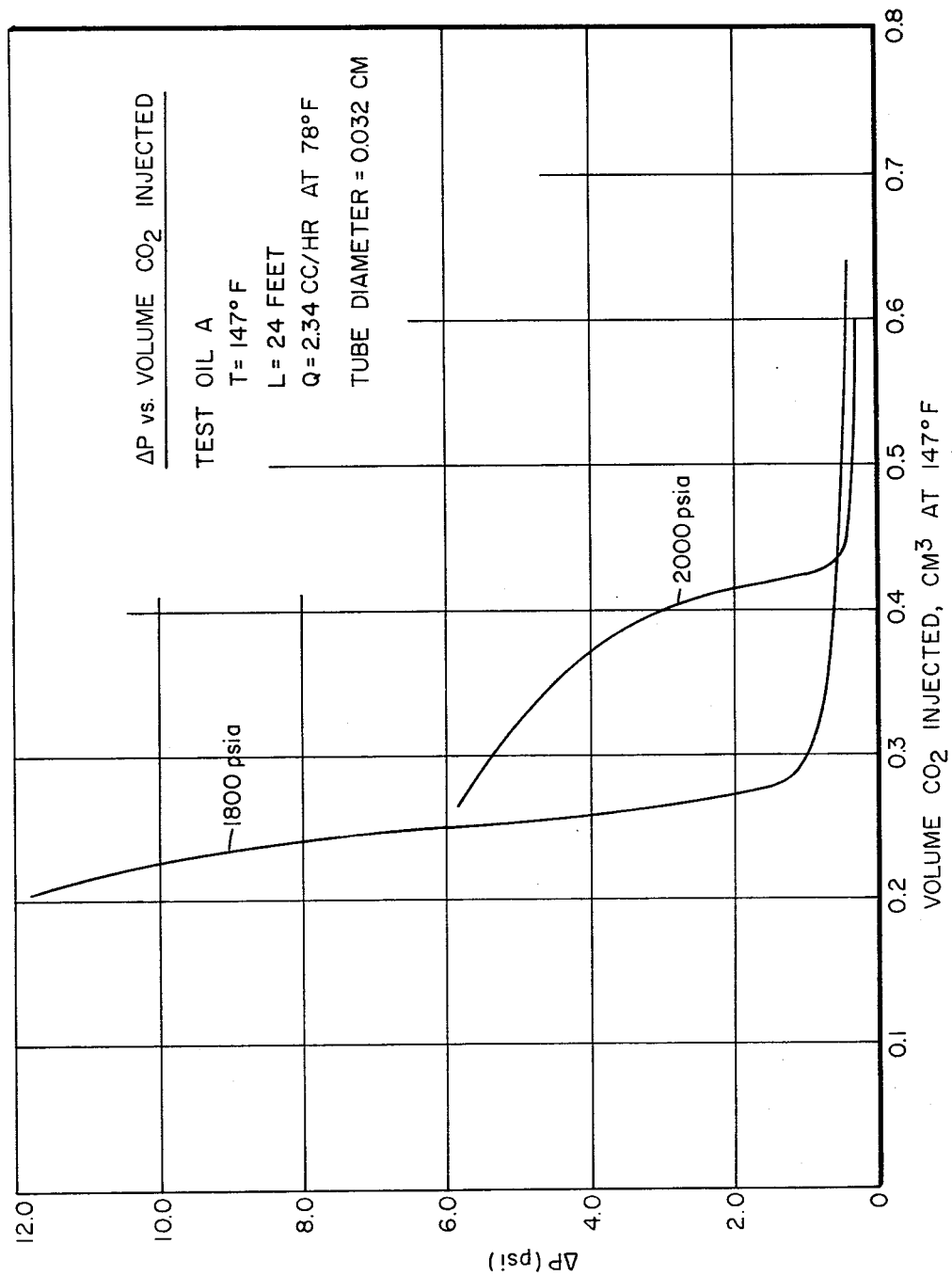
FIG. 4 is a graph showing the pressure drop across a capillary tube as a function of the volume of carbon dioxide injected for immiscible displacement of test oil A at a test temperature of 147° F., a volumetric $CO_2$ flow rate of 2.34 cc/hr at room temperature (78° F.), and pressures of 1821 psia and 2022 psia.
Figure 5:
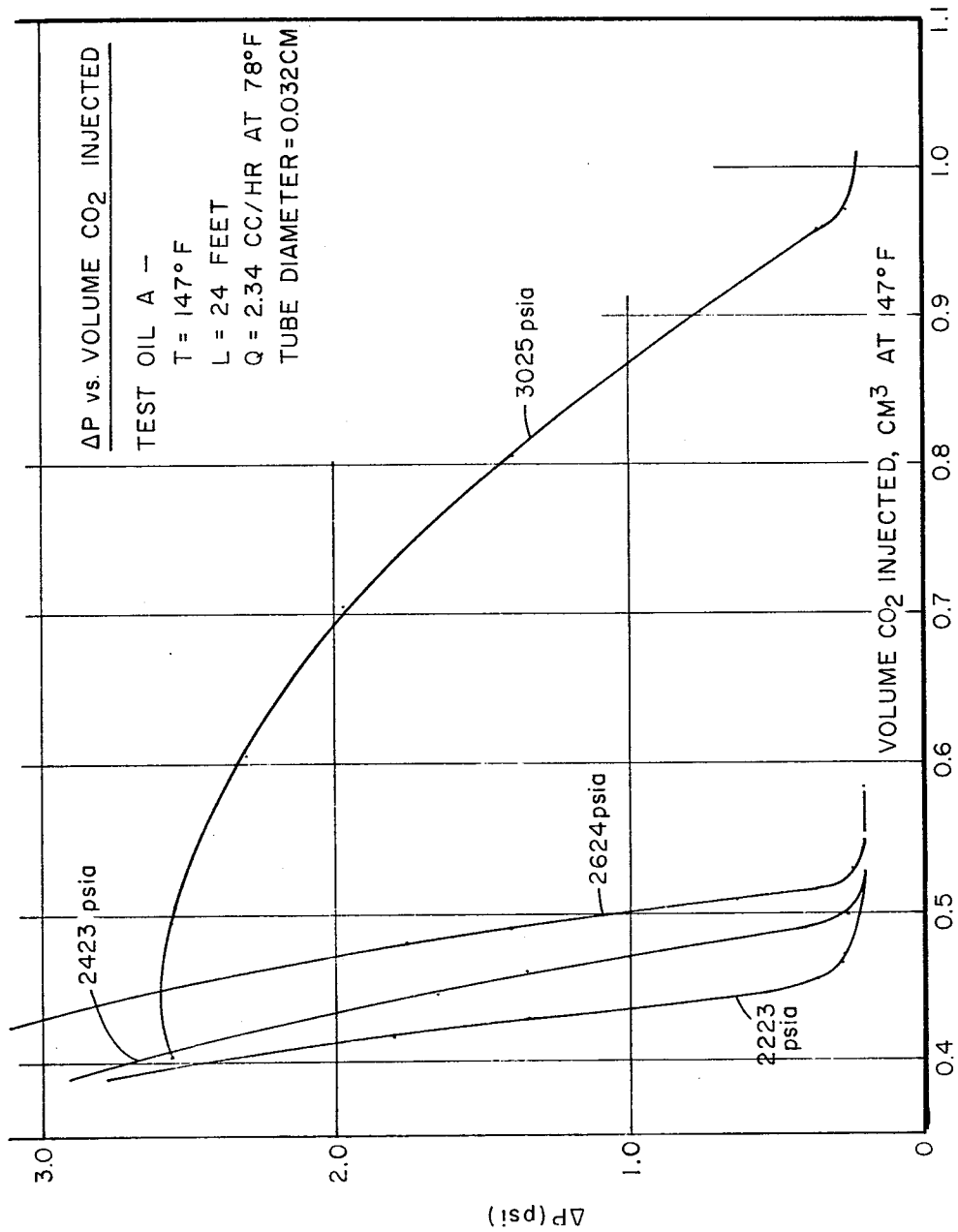
FIG. 5 is a graph showing the pressure drop as a function of the volume of carbon dioxide injected across a capillary tube for miscible displacement of test oil A at a test temperature of 147° F., a volumetric $CO_2$ flow rate of 2.34 cc/hr at room temperature (78° F.), and pressures of 2223, 2423, 2624 and 3025 psia.

FIGS. 4 and 5 show the relationship between pressure drop and volume of $CO_2$ injected for immiscible displacement runs at pressures of 1821 psia and 2022 psia. Using this plot, the pressure drop at the inflection point ($\Delta P_{IP}$) is 4.94 psi at 1821 psia and 0.74 psi at 2022 psia.

FIG. 6 shows the relationship between pressure drop and volume of $CO_2$ injected for miscible displacement runs for pressures of 2223 psia, 2423 psia, 2624 psia and 3025 psia. Using this plot, the pressure drop at the inflection point ($\Delta P_{IP}$) is 0.37 psi for a test pressure of 2223 psia, 0.41 for 2423 psia, 0.29 for 2624 psia, and 0.18 for 3025 psia.

Table 1, below, lists the results of the six runs shown in FIGS. 4 and 5, including mass and volumetric $CO_2$ flow rate data as well as the pressure drop of pure $CO_2$ across the capillary tube under the corresponding test conditions of temperature, flow rate, and pressure.

TABLE 1

| $P_1$ psia | $CO_2$ mass flow rate, g/hr. | $CO_2$ vol. flow rate, cm³/hr. | $\Delta P_{IP}$ psi | $\Delta P_{CO_2}$ psi | $\Delta(\Delta P)$* psi |
|---|---|---|---|---|---|
| 1821 | 2.01 | 4.71 | 4.94 | 0.17 | 4.77 |
| 2022 | 2.05 | 3.97 | 0.74 | 0.17 | 0.57 |
| 2223 | 2.08 | 3.58 | 0.37 | 0.18 | 0.19 |
| 2423 | 2.10 | 3.35 | 0.41 | 0.19 | 0.22 |
| 2624 | 2.13 | 3.20 | 0.29 | 0.19 | 0.10 |
| 3025 | 2.17 | 3.02 | 0.18 | 0.20 | −0.02 |

*$\Delta(\Delta P) = \Delta P_{IP} - \Delta P_{CO_2}$

In order to determine the $CO_2$ MMP, the pressure drop at the point of inflection must be corrected by subtracting the pressure drop across the capillary tube for pure carbon dioxide injected under the same test conditions thereby resulting in a $\Delta(\Delta P)$. The pressure drop for pure carbon dioxide is determined by the following Hagen-Poiseuille equation:

$$\Delta P_{CO_2} = \frac{F_v(8)(\mu)(L)}{\pi (R^4)}$$

where
$\Delta P_{CO_2}$ = pressure drop across capillary tube;
Fv = volumetric flow rate;
$\mu$ = viscosity of $CO_2$ at test temperature and pressure;
L = capillary tube length;
R = capillary tube radius.

To finally determine the $CO_2$ MMP, the results of $\Delta(\Delta P)$ are plotted as a function of pressure as shown in FIG. 6. Using this plot, the $CO_2$ MMP is located graphically as the point of intersection between the two lines that define miscible and immiscible displacement which corresponds to the lowest pressure level at which miscible displacement occurs. As shown in FIG. 6, this point corresponds to a $CO_2$ MMP of 2042 psia for the test oil evaluated.

A comparison of the $CO_2$ MMP for test oil A as determined by the capillary tube method of the present invention with the $CO_2$ MMP for the same oil as determined by the slim tube method previously described is shown in Table 2.

TABLE 2

| | | $CO_2$ MMP, psia | |
|---|---|---|---|
| | Temp. °F. | Slim Tube | Capillary Tube |
| Test Oil A | 147 | 2090 ± 50 | 2042 |

The similarity of the resulting $CO_2$ MMP pressures indicate that the present method is a reliable method for determining the $CO_2$ MMP of a reservoir oil.

Although the method of the present invention has been described in terms of two test pressures above and below the $CO_2$ MMP, it is to be understood that more than two pressures may be employed.

From the foregoing specification one skilled in the art can readily ascertain the essential features of this invention and without departing from the spirit and scope thereof can adapt it to various diverse applications. It is our intention and desire that our invention be limited only by those restrictions or limitations as are contained in the claims appended immediately hereinafter below.

What is claimed is:

1. A method of determining the $CO_2$ minimum miscibility pressure (MMP) of a reservoir oil comprising:
   (a) filling a capillary tube having a predetermined length and diameter with said oil and maintaining the oil at a predetermined temperature $T_1$ and pressure $P_1$ below the $CO_2$ MMP;
   (b) injecting carbon dioxide into the capillary tube at a predetermined flow rate and temperature to displace said oil through said tube while maintaining the oil in the capillary tube at the predetermined temperature $T_1$ and pressure $P_1$ below the $CO_2$ MMP;
   (c) constantly determining the pressure drop across the capillary tube and the total volume of carbon dioxide injected;
   (d) plotting the pressure drop versus volume of carbon dioxide injected data and determining the pressure drop $\Delta P_1$ at the inflection point of the plot at the point where the second derivative goes from a negative value to a positive value;
   (e) repeating steps (a) thru (d) at a pressure $P_2$ below the $CO_2$ MMP to determine the pressure drop $\Delta P_2$ at the inflection point defined in step (d);
   (f) repeating steps (a) thru (d) at a pressure $P_3$ above the $CO_2$ MMP to determine the pressure drop $\Delta P_3$ at the inflection point defined in step (d);
   (g) repeating steps (a) thru (d) at a pressure $P_4$ above the $CO_2$ MMP to determine the pressure drop $\Delta P_4$ at the inflection point defined in step (d);
   (h) calculating the pressure drop $\Delta P_{CO_2}$ across the capillary tube for carbon dioxide at the test conditions for $P_1$, $P_2$, $P_3$ and $P_4$ in accordance with the following Hagen-Poiseuille equation:

$$\Delta P_{CO_2} = \frac{F_v(8)(\mu)(L)}{\pi (R^4)}$$

where
$\Delta P_{CO_2}$ = pressure drop across capillary tube;
Fv = volumetric flow rate;
$\mu$ = viscosity of $CO_2$ at test temperature and pressure;
L = capillary tube length;
R = capillary tube radius.
   (i) subtracting the pressure drop for carbon dioxide corresponding to pressure $P_1$, $P_2$, $P_3$ and $P_4$ from the corresponding pressure drop $\Delta P_1$, $\Delta P_2$, $\Delta P_3$ and $\Delta P_4$ to obtain a resultant pressure drop $\Delta(\Delta P)_1$, $\Delta(\Delta P)_2$, $\Delta(\Delta P)_3$ and $\Delta(\Delta P)_4$;

(j) plotting $\Delta(\Delta P)_1$ and $\Delta(\Delta P)_2$ as a linear function of $P_1$ and $P_2$ for immiscible $CO_2$ displacement;

(k) plotting $\Delta(\Delta P)_3$ and $\Delta(\Delta P)_4$ as a linear function of $P_3$ and $P_4$ for miscible $CO_2$ displacement; and (l) determining the $CO_2$ MMP graphically by determining the pressure at the point where the two lines defining miscible and immiscible displacement intersect.

2. The method of claim 1 wherein the predetermined temperature of the carbon dioxide is at room temperature.

3. The method of claim 1 where the predetermined flow rate of carbon dioxide is 2.34 cc/hr. at 78° F.

4. The method of claim 1 where the capillary tube is coiled stainless steel, 24 feet long and 0.032 cm. in diameter.

5. The method of claim 1 wherein the temperature of the oil in the capillary tube is maintained at a temperature within the range of 80° to 250° F., the pressure within the range of 1000 to 4000 psi, and the flow rate within the range of 0.97 to 2.34 cc/hr at room temperature.

6. The method of claim 1 wherein the $CO_2$ displacement tests for a given test oil at a fixed temperature and $CO_2$ displacement rate are conducted at more than two pressure levels above and below the $CO_2$ MMP.

7. A method of determining the $CO_2$ minimum miscibility pressure (MMP) of a reservoir oil comprising:

(a) filling a capillary tube having a predetermined diameter and length with said oil;

(b) maintaining said oil in said tube at a predetermined temperature $T_1$ and a predetermined pressure $P_1$ less than the MMP;

(c) injecting carbon dioxide into the inlet end of said tube at a predetermined volumetric flow rate at room temperature to displace the oil through the tube while maintaining the pressure on the oil at $P_1$ and the oil temperature at $T_1$;

(d) constantly determining the pressure drop between the inlet and outlet end of the tube and the total volume of carbon dioxide injected;

(e) plotting the pressure drop versus volume of carbon dioxide injected data for $P_1$ and determining the pressure drop $\Delta P_1$ at the inflection point of the plot where the second derivative goes from a negative value to a positive value;

(f) flushing said tube with a solvent, drying said tube with a gas, and evacuating said tube;

(g) filling said tube with a fresh sample of said oil;

(h) maintaining said oil in said tube at said predetermined temperature $T_1$ and at a predetermined pressure $P_2$ less than the $CO_2$ MMP;

(i) injecting carbon dioxide into the inlet end of said tube at a predetermined flow rate equal to that of step (c) to displace oil through the tube while maintaining the pressure on the oil at $P_2$ and the oil temperature at $T_1$;

(j) repeating step (d);

(k) plotting the pressure drop versus volume of carbon dioxide data for $P_2$ and determining the pressure drop $\Delta P_2$ at the inflection point of the plot where the second derivative goes from a negative value to a positive value;

(l) repeating steps (f) and (g);

(m) maintaining said oil in said tube at said predetermined temperature $T_1$ and at a predetermined pressure $P_3$ greater than the $CO_2$ MMP;

(n) injecting carbon dioxide into the inlet end of said tube at the predetermined flow rate equal to step (c) to displace oil through the tube while maintaining the pressure on the oil at $P_3$ and the oil temperature at $T_1$;

(o) repeating step (d);

(p) plotting pressure drop versus volume of carbon dioxide injected data at $P_3$ and determining the pressure drop $\Delta P_3$ at the inflection point of the plot where the second derivative goes from a negative value to a positive value;

(q) repeating step (f) and (g);

(r) maintaining said oil in said tube at said predetermined temperature $T_1$ and at a predetermined pressure $P_4$ greater than the $CO_2$ MMP;

(s) injecting carbon dioxide into the inlet end of said tube at the predetermined flow rate equal to step (c) to displace oil through the tube while maintaining the pressure at $P_4$ and the oil temperature at $T_1$;

(t) repeating step (d);

(u) plotting the pressure drop versus volume of carbon dioxide injected data $P_4$ and determining the pressure drop $\Delta P_4$ at the inflection point of the plot occurring at the point where the second derivative goes from a negative value to a positive value;

(v) calculating the pressure drop $\Delta P_{CO_2}$ for carbon dioxide under the same conditions of temperature $T_1$, flow rate, and pressure according to step (c) for P1, P2, P3 and P4 in accordance with the following Hagen-Poiseuille equation:

$$\Delta P_{CO_2} = \frac{F_v(8)(\mu)(L)}{\pi (R^4)}$$

where
$\Delta P_{CO_2}$ = pressure drop across tube;
$F_v$ = volumetric flow rate;
$\mu$ = viscosity of $CO_2$ at test temperature and pressure;
$L$ = capillary tube length;
$R$ = capillary tube radius.

(w) calculating $\Delta(\Delta P)_1$ by subtracting $\Delta P_{CO_2}$ at $P_1$ from $\Delta P_1$;

(x) calculating $\Delta(\Delta P)_2$ by subtracting $\Delta P_{CO_2}$ at $P_2$ from $\Delta P_2$;

(y) calculating $\Delta(\Delta P)_3$ by subtracting $\Delta P_{CO_2}$ at $P_3$ from $\Delta P_3$;

(z) calculating $\Delta(\Delta P)_4$ by subtracting $\Delta P_{CO_2}$ at $P_4$ from $\Delta P_4$;

(aa) plotting said pressure difference $\Delta(\Delta P)_1$ and $\Delta(\Delta P)_2$ as a linear function of $P_1$ and $P_2$ for immiscible $CO_2$ displacement;

(bb) plotting said pressure difference $\Delta(\Delta P)_3$ and $\Delta(\Delta P)_4$ as a linear function of $P_3$ and $P_4$ for miscible $CO_2$ displacement; and (cc) determining the $CO_2$ MMP graphically as the pressure at the point where the two lines defining miscible and immiscible displacement intersect.

8. The method of claim 7 wherein the predetermined temperature of the carbon dioxide is at room temperature.

9. The method of claim 7 where the predetermined flow rate of carbon dioxide is 2.34 cc/hr. at 78° F.

10. The method of claim 7 where the capillary tube is coiled stainless steel, 24 feet long and 0.032 cm. in diameter.

11. The method of claim 7 wherein the temperature of the oil in the capillary tube is maintained at a temperature within the range of 80° to 250° F., the pressure within the range of 1000 to 4000 psi, and the flow rate within the range of 0.97 to 2.34 cc/hr at room temperature.

12. The method of claim 7 wherein the $CO_2$ displacement tests for a given test oil at a fixed temperature and $CO_2$ displacement rate are conducted at more than two pressure levels above and below the $CO_2$ MMP.

13. An apparatus for determining the $CO_2$ minimum miscibility pressure (MMP) of a reservoir oil comprising:
 (a) an elongated capillary tube having an inlet end and an outlet end;
 (b) means for delivering a stream of oil to the inlet end of the tube;
 (c) an expansion chamber having a top and bottom;
 (d) conduit means for providing fluid communication between the top of said chamber and the outlet end of said tube;
 (e) back pressure regulator means in the bottom of said chamber for maintaining a predetermined pressure on said chamber;
 (f) means for maintaining said tube at a constant temperature;
 (g) means for injecting carbon dioxide into the inlet end of said tube at a constant flow rate to displace oil through the tube and into said expansion chamber; and
 (h) means for constantly measuring the pressure difference between the inlet and outlet end of the tube and the total volume of carbon dioxide injected into the tube.

14. The apparatus of claim 13 further comprising means for flushing, drying, and evacuating the system.

15. The apparatus of claim 13 wherein said capillary tube comprises a coiled stainless steel tube having a diameter of about 0.032 cm. and a length of 24 feet.

16. An apparatus for determining the $CO_2$ minimum miscibility pressure (MMP) of a reservoir oil comprising:
 (a) an elongated capillary tube having an inlet end and an outlet end;
 (b) a first expansion chamber having a top and bottom;
 (c) valve means for supplying oil from the top of said chamber to the inlet end of said tube;
 (d) means vertically movable in sealing engagement with the internal walls of said chamber for conveying oil from the top of said chamber to the inlet end of said tube;
 (e) means for conveying fluid to the bottom of said chamber causing the vertically movable means in sealing engagement with the internal walls of said chamber to move in response to said fluid thereby conveying oil from said chamber to the inlet end of said tube;
 (f) means for maintaining said tube at a constant temperature;
 (g) a second expansion chamber having a top and bottom;
 (h) conduit means for providing fluid communication between the top of said second chamber and the outlet end of said tube;
 (i) means vertically movable in sealing engagement with the internal walls of said chamber;
 (j) back pressure regulator means in the bottom of said second chamber for maintaining a predetermined pressure on the second chamber;
 (k) a third expansion chamber containing carbon dioxide having a top and bottom;
 (l) valve means for supplying carbon dioxide from the top of said third chamber and the inlet end of said tube;
 (m) means for conveying said carbon dioxide from said third chamber to the inlet end of said tube at a constant rate thereby displacing the oil through the tube; and
 (n) means for constantly measuring the pressure difference between the inlet and outlet end of the tube and the total volume of carbon dioxide injected into the tube; and 17. The apparatus of claim 16 further comprising means for flushing, drying, and evacuating the system.

18. The apparatus of claim 16 further comprising valve means adapted to isolate fluid between the inlet and outlet end of the tube.

19. The apparatus of claim 16 wherein said capillary tube comprises a coiled stainless steel tube having a diameter of about 0.032 cm. and a length of 24 feet.

* * * * *